United States Patent
Prokoski

(10) Patent No.: US 6,496,594 B1
(45) Date of Patent: Dec. 17, 2002

(54) METHOD AND APPARATUS FOR ALIGNING AND COMPARING IMAGES OF THE FACE AND BODY FROM DIFFERENT IMAGERS

(76) Inventor: Francine J. Prokoski, 5410 Colchester Meadow La., Fairfax, VA (US) 22030

( * ) Notice: Subject to any disclaimer, the term of this patent is extended or adjusted under 35 U.S.C. 154(b) by 0 days.

(21) Appl. No.: 09/422,273

(22) Filed: Oct. 21, 1999

Related U.S. Application Data

(60) Provisional application No. 60/105,217, filed on Oct. 22, 1998.

(51) Int. Cl.$^7$ .................................................. G06F 9/00
(52) U.S. Cl. ........................ 382/118; 382/118; 382/125; 382/294
(58) Field of Search .................. 382/115–118, 124–126, 382/299–300, 276, 278; 463/29; 235/380

(56) References Cited

U.S. PATENT DOCUMENTS

| | | | | |
|---|---|---|---|---|
| 4,975,969 A | * | 12/1990 | Tai | 382/116 |
| 5,163,094 A | | 11/1992 | Prokoski et al. | |
| 5,775,806 A | * | 7/1998 | Allred | 374/124 |
| 5,825,941 A | * | 10/1998 | Linford | 382/294 |
| 5,926,555 A | * | 7/1999 | Ort et al. | 382/124 |
| 6,049,621 A | * | 4/2000 | Jain et al. | 382/125 |
| 6,072,895 A | * | 6/2000 | Bolle et al. | 382/125 |
| 6,134,340 A | * | 10/2000 | Hsu et al. | 382/124 |
| 6,142,876 A | * | 11/2000 | Cumbers | 463/25 |
| 6,173,068 B1 | * | 1/2001 | Prokoski | 382/115 |

* cited by examiner

*Primary Examiner*—Jose L. Couso
*Assistant Examiner*—Gregory Desire
(74) *Attorney, Agent, or Firm*—Lawrence E. Laubscher, Jr.

(57) ABSTRACT

A method and apparatus for comparing an infrared image of a person to a database of visual images of persons and calculating the probability that each is a match to the infrared image is characterized by extracting minutiae from the infrared image and extracting visible minutiae from the visible images. Coincident minutiae which occur in both spectra are used to scale and register the infrared and the visible images. Other minutiae are spectrum-dependent, but must obey rules relative to minutiae of the other spectrum, due to the anatomical structure of the human face and body. The primary application is for identification of persons seen in infrared surveillance imagery, using a reference database of visual images. Other applications include compression of talking head video and animation of synthetic faces. The method and apparatus can also be applied to areas of the body other than the face, to compare images from different spectra including images from medical sensors.

11 Claims, 12 Drawing Sheets

METHOD AND APPARATUS FOR ALIGNING AND COMPARING IMAGES OF THE FACE AND BODY FROM DIFFERENT IMAGERS

This application claims the benefit of provisional application No. 60/105,217 filed Oct. 22, 1998.

BACKGROUND OF THE INVENTION

There are common features between infrared (IR) and visual images of the human body. Using the face as an example, head shape and size, and the relative location, shape, and size of features such as the eyes, mouth, and nostrils are the same in both imaging modes. A database of images can be segmented into classes using metrics derived from those common features, and the same classification will be obtained from either visual or infrared images. Height can be also used as a classification measure when it can be inferred from the collected image or from separate sensor data. An infrared image of an unclothed area of the body, such as the face, presents much more detailed and person-specific information than does a visible image. However, visible images are more commonly collected and large historical databases of visual images exist. It is therefore desirable to automate a process for comparing imagery from both the visual and infrared modes.

Infrared images are unique to each person, even for identical twins. Visual images are not unique because many people look similar and can disguise themselves to look enough like one another that an automated identification system cannot distinguish them. Therefore, in a large database, it is not possible to automatically perform a one-to-one linkage between infrared and visual images because the visual images are not sufficiently unique. However, for each infrared image, an automated system can eliminate all visual images which cannot be a match due to insufficient correspondence between minutiae characteristics. In general, it is estimated that more than 95% of a visual database can be eliminated as a match to a given infrared image. This has application to the use of infrared surveillance cameras to identify wanted persons for whom only visual images are on file. The infrared-visual matching system compares each person it sees in infrared and classifies him as either a possible match to someone on the visual image watch list or not a match. Persons who are possible matches can then receive greater attention from immigration or security authorities. This allows the use of infrared surveillance imagery to proceed without waiting until a large database of infrared images is established.

The use of infrared imagery also provides for the detection of disguises, whether worn or surgical, which may not be detectable from visible imagery. For example, artificial facial hair such as a mustache is readily detectable in an infrared image although it appears natural in visible images. The fact that infrared surveillance imagery shows a man with a fake mustache provides a clue to consider in matching against a visible image database. Surgical disguises such as a face lift leave telltale short and longer term variations in the facial thermogram, while the visual image may appear to be a different person and show no sign of surgery, The ability to detect in IR images that surgical changes have been made to a particular area of the face permits an automated system to broaden the parameters for searching for possible matching visual images in an historical database.

High definition visual images of the face and body are routinely produced and stored for medical, diagnostic and forensic use. Common examples are the photographing of criminal suspects through booking stations producing "mug shots", driver's license photographs produced by each state, and passport photos used by the State Department. Many such large facial image databases exist, in hardcopy and in electronic form, and there is increasing research ongoing into automated matching of newly taken images with those databases. For example, there are frequent attempts to match surveillance images of a person using a stolen credit card at an ATM with photographs of persons previously convicted of similar crimes.

Visual imagery, particularly from surveillance cameras, is often of poor quality due to dim illumination at the scene. Low light level or infrared cameras are expected to become more widely used for surveillance as their cost diminishes. There is therefore a need to correlate between newly acquired infrared images and existing databases of video images. Even in the future, when simultaneous collection of video and IR images will generate correlated databases, there will always be a need to match images taken in one spectral domain with images taken in another. This can include matching images taken in one IR band (such as 3–5 micron) with images taken in another IR band (such as 8–12 micron).

Since IR cameras are passive, emitting no radiation and therefore presenting no health hazards, they may be used in conjunction with other imaging medical devices such as x-ray, sonogram, CAT scan devices, etc. Minutiae derived from the IR image may then be superimposed or annotated onto the resulting medical image. This presents a standard technique for generating standardized reference points on all medical imagery. Subsequently, the method and apparatus of this invention can be used to search a database of annotated medical images to find a match with a current IR image or current medical image annotated with IR minutiae.

Regions of Interest (ROI) may be utilized instead of minutiae, where the ROI may be elemental or other shapes including fractal or wavelet-derived structures, segments of blood vessels, locations underneath or otherwise relative to tattoos, moles, freckles, or other distinguishable features, or wiremesh or finite elements used for thermodynamic or visible modeling of the body. Rules may relate the shapes and positions of such elements, their centroids and other features. Time sequences of minutiae and ROIs may be compared, with the decision as to a possible match made on the basis of cumulative thresholds and rule tolerances over the sequence.

Facial expression and speech modeling has application to synthetic videoconferencing and face animation. Substantial bandwidth and storage reduction can result. Use of IR minutiae offers more precise modeling than current use of visual images. The present invention provides a technique by which IR images can be tied to the visual image being displayed.

BRIEF DESCRIPTION OF THE PRIOR ART

The identification of persons from infrared images is known in the art as evidenced by the Prokoski et al U.S. Pat. No. 5,163,094 which discloses a method and apparatus for analyzing closed thermal contours, called "elemental shapes" which are created by the vascular system interacting with the anatomical structure. Fifty or more elemental shapes can be identified for example in a human face imaged with an IR camera which has an NETD (noise equivalent thermal difference) of 0.07° C. and a spatial resolution of 256×256 pixels. Characteristics of those shapes, such as the centroid location and ratio of area to perimeter, remain relatively constant regardless of the absolute temperature of the face, which varies with ambient and physiological conditions. Two infrared images are compared by comparing the characteristics of corresponding shapes. A distance metric is defined and calculated for each pair of images. If the value is within a threshold, the two images are considered to be from the same person.

In the Prokoski et al U.S. patent application Ser. No. 08/514,456, there is disclosed a method and apparatus for extracting and comparing thermal minutiae corresponding to specific vascular and other subsurface anatomical locations from two images. Minutiae may be derived from thermal contours, or may be absolutely associated with specific anatomical locations which can be seen in the thermal image, such as the branching of blood vessels. Each minutia is then associated with a relative position in the image and with characteristics such as apparent temperature, the type of branching or other anatomical feature, vector directions of the branching, and its relation to other minutiae.

The comparison of thermal minutiae from two facial images is analogous to the comparison of sets of fingerprint minutiae, in that two images are said to identify the same person if a significant subset of the two sets are found to correspond sufficiently in relative positions and characteristics. Classification of the facial thermograms can be performed to partition a database and reduce the search for matching facial patterns. Alternately, encoding of the minutiae patterns offers a unique FaceCode which may be repeatably derived from each person, minimizing the need for searching a database.

Infrared imaging can be used to locate minutiae points over the entire body surface which correspond to specific anatomical locations such as intersection points and branch points of the underlying blood vessels. The thermal minutiae technique and apparatus utilizes a built-in set of whole-body registration points viewable in IR on the face and body surface. The registration points can then be used to compare infrared images taken with different equipment at different times of different people and under different conditions to facilitate comparison of those images.

The IR camera is totally passive, emitting no energy or other radiation of its own, but merely collecting and focusing the thermal radiation spontaneously and continuously emitted from the surface of the human body. Current IR cameras operating in the mid to long wavelength region of 3–12 microns, record patterns caused by superficial blood vessels which lay up to 4 cm below the skin surface. Future cameras will have increased sensitivity which will translate into even more defined minutiae. With current IR cameras, approximately 175 thermal facial minutiae may be identified in thermal images from superficial blood vessels in the face. More than 1000 thermal minutiae may be identified over the whole body surface. Using more sensitive infrared cameras, additional minutiae from deeper vascular structures may be identified in the thermal images.

The normal body is basically thermally bilaterally symmetric. Side to side variations are typically less than 0.25 degrees Celsius. This fact is used in assigning axes to the body's image. Where the skin surface is unbroken, there is a gradual variation of temperatures across blood vessels, with the highest temperatures across the body surface being directly on top of major blood vessels. Major thermal discontinuities occur at entrances to body cavities such as the eye sockets, nostrils, or mouth. These provide global reference points for automatic orientation of the thermal image. Local and relatively minor discontinuities in the skin surface occur at scars, moles, burns, and areas of infection. The thermal surface can be distorted through pressures and activities such as eating, exercising, wearing tight hats and other clothing, sinus inflammation, infection, weight gain and loss, and body position. However, the minutiae points remain constant with respect to their position relative to the underlying anatomy.

The technique for thermal minutiae extraction and matching can be summarized as follows:

1. The current thermal image is digitized.
2. The current image is divided into pixels, where the size of the pixel relates to the resolution or quality of the result desired.
3. Certain pixels are selected as minutiae points.
4. Each minutia is assigned characteristics such as one or more vectors having magnitude and directional information in relation to the surrounding areas of the thermal image about that minutia, absolute or relative temperature at or around the minutia location, shape of the surrounding thermal area or areas, curvature of the related shape or shapes, size of the surrounding shape or shapes, location of the minutia relative to the body, distance to other minutiae, vector length and direction to other minutiae, number of crossings of thermal contours between it and other minutiae, number of other minutiae within a certain range and direction, the type of minutiae such as the apparent end point of a blood vessel, a point of maximum curvature of a thermal contour, all points on an anatomical element such as a blood vessel which can be distinguished by thresholding or range gating or focusing the thermal camera or image, the centroid of a lymph node, or the centroid or other reference of an anatomical structure with distinguishing thermal capacitance. Either active or passive infrared imaging can be used. For active imaging, the subject can be subjected to heat or cold by external application of hot or cold air, illumination, dehumidification, ingestion of hot or cold foodstuffs, or ingestion of materials which cause vasodilation or vasoconstriction.
5. A set of minutiae characteristics of the current image is compared by computer to the set of minutiae characteristics of other images.
6. The comparison results are used to determine corresponding minutiae from the two images, and to morph or mathematically adjust one image with respect to the other to facilitate comparison.
7. The differences between the current image and database images are computed for the entire image or for areas of interest.
8. The differences are compared to a threshold and image pairs which exceed the threshold are considered impossible matches.

Infrared facial minutiae maybe derived from elemental shapes (such as by using the centroids of each shape or the zero locations resulting from wavelet compression and expansion). Particularly when high quality infrared images are used, absolute minutiae can be directly extracted without the computationally intensive analysis required for template or shape comparisons.

It is also known in the prior art to compare visible images through fiducial points involving definition of face metrics which may be considered to have aspects in common with the present invention. For example, the Tal U.S. Pat. No. 4,975,969 discloses a method and apparatus for uniquely identifying individuals by measurement of particular physical characteristics viewable by the naked eye or by imaging in the visible spectrum. Tal defined facial parameters which are the distances between identifiable parameters on the human face, and/or ratios of the facial parameters, and used them to identify an individual since he claims that the set of parameters for each individual is unique. Particular parameters such as the distance between the eye retina, the distance from each eye retina to the nose bottom and to the mouth center, and the distance from the nose bottom to the mouth center are set forth, as they may be particularly defined due to the shadowed definable points at each end.

The approach disclosed in the Tal patent utilizes visible features on the face from which a unique set of measurements and ratios allegedly can be developed for each individual. This approach is not particularly satisfactory, nor does it pertain to identical twins. In addition, the "rubber sheeting" effect caused by changes in facial expression, the aging effects which cause lengthening of the nose, thinning of the lips, wrinkles, and deepening of the creases on the sides of the nose, would all cause changes in the parameters and in their ratios. Therefore, very few measurements which can be made on a human face are constant over time, and the paucity of such constant measurements makes it improbable that facial metrics in visible images can be useful for identification of sizable populations. The Tal patent does not deal with comparison of images from other than visible detectors, and so does not consider the specific focus of the present invention which is the comparison of images from different spectral bands. Moreover, the Tal patent does not specifically caution about varying lighting conditions, which could severely limit the utility of the technique, even for classification.

Visible face metrics may be useful as a classification technique, but the visible features can be modified cosmetically or surgically without detection, resulting in misclassification. By contrast, the technique of the present invention utilizes hidden micro parameters which lie below the skin surface, and which cannot be forged. The current patent's use of underlying features which are fixed into the face at birth and remain relatively unaffected by aging provides for less inherent variability in the values of the parameters over time than is provided by the prior art.

Visible metrics require ground truth distance measurements unless they rely strictly upon ratios of measurements. They can be fooled by intentional disguises, and they are subject to variations caused by facial expressions, makeup, sunburns, shadows and similar unintentional disguises. Detecting disguises and distinguishing between identical twins may or may not be possible from visible imagery if sufficient resolution and controlled lighting is available. However, the level of resolution which may be required significantly increases the computational complexity of the identification task, and makes the recognition accuracy vulnerable to unintentional normal variations.

The use of eigenanalysis of visual faces to develop a set of characteristic features is disclosed in Pentland (MIT Media Laboratory Perceptual Computing Section, Technical Report No. 245 View-Based and Modular Eigenspaces for Face Recognition). Faces are then described in terms of weighting of those features. The approach claims to accommodate head position changes and the wearing of glasses, as well as changes in facial expressions. A representative sample of 128 faces was used from a database of 7,562 images of approximately 3000 people. A principal components analysis was performed on a representative sample. The first 20 eigenvectors were used. Each image was annotated by hand as to sex, race, approximate age, facial expression, etc. Pentland does not deal with comparing images from different spectral bands. Nor does his technique perform well in the case of visible images obtained under differing lighting conditions.

Pentland discloses that pre-processing for registration is essential to eigenvector recognition systems. The processing required to establish the eigenvector set is extensive, especially for large databases. Addition of new faces to the database requires the re-running running of the eigenanalysis. Pentland and other "eigenface" approaches are database-dependent and computationally intensive. In contrast, the proposed minutiae comparison of the present invention is independent of the database context of any two images. Minutiae are directly derived from each image, visible or IR, and compared using fixed rules, regardless of the number or content of other images in the database.

An approach for comparing two sets of image feature points to determine if they are from two similar objects is disclosed in Sclaroff (Sclaroff and Pentland: MIT Media Laboratory, Perceptual Computing Technical Report #304). He suggests that first a body-centered coordinate frame be determined for each object, and then an attempt be made to match up the feature points. Many methods for finding a body-centered frame have been suggested, including moment of inertia methods, symmetry finders, and polar Fourier descriptors. These methods generally suffer from three difficulties: sampling error; parameterization error; and non-uniqueness.

Sclaroff introduces a shape description that is relatively robust with respect to sampling by using Falerkin interpolation, which is the mathematical underpinning of the finite element method. Next, he introduces a new type of Galerkin interpolation based on Gaussians that allow efficient derivation of shape parameterization directly from the data. Third, he uses the eigenmodes of this shape description to obtain a canonical, frequency-ordered orthogonal coordinate system. This coordinate system is considered the shape's generalized symmetry axes. By describing feature point locations in the body-centered coordinate system, it is straight-forward to match corresponding points, and to measure the similarity of different objects.

Applicant has previously utilized a principal components analysis of thermal shapes found in facial thermograms. The resulting accuracy of 97% from IR images equals or surpasses the results reported by Pentland with visible facial images. Applicant's training database, furthermore, included identical twins and involved non-cooperative imaging of about 200 persons. Thus, the head sizes and orientations were not pre-determined as they were in the Pentland study. As a result, the use of eigenanalysis of thermal shapes is more robust than the use of eigenanalysis of visual facial features. However, the basic requirements of eigenanalysis still pertain to their use in matching of thermal images by consideration of inherent elemental shapes. That is, the approach is computationally intensive, requires a pre-formed database, and requires standardization of the images through pre-processing.

The present invention differs from prior visible and IR recognition approaches in that it does not merely sample a finite number of points on an image grid; it extracts points which have particular meaning in each spectrum and automatically distinguishes between cross-spectrum minutiae which are coincident and those which are related by rules associated with anatomical bases. It assigns a difference or feature space distance to each pair of coincident minutiae, with a total distance calculated over all such pairs. This first step may be used to eliminate candidate matches which produce distances above a threshold. Then the spectrum-dependent minutiae are compared relative to anatomical rules to further eliminate impossible candidate matches. The prior art has not addressed alignment and comparison of visual/IR or IR/IR human images based upon anatomical rules and the characteristics of features viewable in the IR image.

SUMMARY OF THE INVENTION

It is a primary object of the present invention to provide a method and apparatus for identifying visual images which may be a match to infrared images of faces or bodies. A thermal image of a portion of the individual's body is generated and is processed to produce a set of minutiae points, together with characteristics which describe each such point and its relation to other minutiae. That combination of minutiae and characteristics is considered unique to the individual and essentially persistent in spite of ambient, physiological, emotional, and other variations which occur on a daily basis. Any portion of the body can be utilized, but the face is preferred due to its availability. Since parts of the face may be blocked by glasses, facial hair, or orientation to the sensor, such as a camera, the system and method allows for identification based on partial faces.

Candidate visual images are processed to extract minutiae characteristic of the subject and the visual spectrum. The IR and visual images are scaled to the same standard and aligned based upon minutiae which are coincident in the two spectra. A measure of the amount of warping required to accomplish the alignment is calculated. Then other spectrum-dependent minutiae are compared, with relation to certain rules which would be met if the two images were of the same person, based upon anatomical structures of the human face and body. A measure of the degree of compliance with the rules is calculated. The decision to include or exclude a given visual image from the class of possible matching images to the infrared image is made based upon these measures relative to thresholds which are established to control possible errors in the system.

Just as locating the center of a fingerprint is essential to certain fingerprint matching algorithms, establishing axes for the facial minutiae is also essential. In an interactive system, human operators establish face axes, similar to fingerprint examiners setting the orientation of latents. A human demarcates the eye pupils, canthi and/or nostrils by manipulating a cursor on the system display. Axes are then automatically generated vertically through the center of mass of the eye pupils or canthi and nostrils and horizontally through the pupils or canthi centroids. If the axes are not perpendicular, the vertical axis can be adjusted to not necessarily bisect the nostrils. The human operator also indicates any unusual features, such as a missing eye or eye patch, wearing of bandages, tattoos, deformation of the lips or other visible gross thermal asymmetries of the face. An automated system can perform these as well.

The unknown face is partitioned into segments, and corresponding segments matched. This will accommodate matching of partial faces when faces are partially disguised or hidden behind other faces in a crowd.

In the full-frontal face, the thermal image is grossly symmetrical bilaterally. The canthi or sinus areas in normal individuals are the hottest extended areas of the face. When glasses are not worn, it is a simple process to locate the canthi in the thermal image and use them to establish axes for the face. Other features which may be used are the nostrils, which may present alternately hot and cold bilaterally symmetric areas as the individual breathes in and out. The horizontal axis may be drawn through the outer corners of each eye, which are readily distinguishable in the infrared images or through the pupils which may be seen in some IR imagery. The vertical axis may then be drawn through the bow of the upper lip, or through the center point of the two nostrils, or at the midpoint between the eye corners. The intersection of the two axes will occur at the center of the two eyes. The midpoint between the horizontal through the eyes is defined as the center of the face.

If the person is wearing glasses, the pattern of the glasses, which block the infrared emissions from the face and thereby produce an extended cold area with sharp cut-off thermally, can be used to approximate the facial axes. If a sufficient number of minutiae are obtainable from portions of the face not blocked by glasses, facial hair, or other concealments, a person may be identifiable. Alternatively, if fewer than a minimum number of minutiae specified for a particular scenario are extracted by an automated system for a particular person, that person may be considered by the system to be a potential match, but be tagged as having a low number of minutiae.

Various perturbations, such as facial expression changes, can distort the relative locations of minutiae points to an extent. This is analogous to the deformations which occur in fingerprints due to movement between the fingers and the print surface. The minutiae matching algorithms allow for variations in the position and characteristics of the minutiae, as well as in the subset of minutiae which are seen due to the field of view of the camera and to possible obstruction of certain areas of the face in the image.

The face surface presents a smooth continuum of thermal levels, and reflects metabolic activity, ambient and internal temperatures, and ambient sources of thermal energy. Discontinuities occur at breaks in the skin continuum, such as caused by the nostrils, the mouth opening, the eyes, facial hair, moles or other skin disturbances, and any applique such as bandages.

According to a preferred embodiment of the invention, minutiae are used from the face. The minutiae are referenced to axes derived from specific physiological features. Although many different approaches may be used to obtain repeatable minutiae from facial thermograms, the preferred approach uses a number of extraction routines to produce a plurality of minutiae sufficient for an intended purpose. Thus, for a relatively low order of required security, on the order of ten minutiae may be extracted using absolute anatomical positions such as branch locations of the carotid and facial arteries.

For a high security requirement, on the order of 100 derived minutiae may be extracted using additional computations to identify further derived and absolute minutiae. The minutiae extraction and characterization procedure locates the position of each minutia. In addition it may note characteristics of each point such as: a vector indicating the orientation of the corresponding blood vessel; a second vector indicating the relative orientation of the branching blood vessel; the normalized apparent temperature; and the apparent width of the corresponding blood vessels. As with some fingerprint minutiae matching machines, use of the characteristics can enhance the speed and accuracy of identification. Furthermore, it can improve the accuracy and speed of automatic fusion of medical imagery.

This basic technique can be employed on an area-by-area basis when portions of the body cannot be seen or when significant changes have occurred in portions of the thermogram such as when portions of the body have suffered external wounds. This would be done by segmenting the thermogram to consider only the portions of the body in which minutiae can be detected. Functionally this is equivalent to matching a latent partial fingerprint found at a crime scene to a full rolled print filed in the FBI system. The set of minutiae points, together with characteristics which describe each such point and its relation to other minutiae is considered unique to the individual and persistent, for both contact fingerprints and thermal minutiae.

Verification that two images from different spectra may be from the same person can be an end goal in itself or the first step in further processing the two images to extract comparison data.

A change in facial expression or the action of speech causes movements in affected areas of the face, particularly the lips, but also the eye, chin, forehead, and cheek areas. Encoding of facial expressions and facial movements during speech is currently being studied for bandwidth reduction in the transmission of "talking head" video for applications such as videophone, videoconferencing, video email, synthetic speech, and face animation. The intent is to transmit a baseline image followed by encoded changes to that image, with reconstruction of the animated face at the receiving end. This process offers significant bandwidth reduction, but may produce imagery in which the talking face seems stiff and unnatural or does not appear to be synchronized with the audio, giving the unacceptable look of a dubbed foreign film.

All such studies involve modeling the facial movements based upon the relocation of certain observable points of the face, such as the corners of the mouth. The various models differ in the extent to which they consider the underlying facial muscles and nerves. There are few observable reference points on a generalized face, especially under uncontrolled lighting conditions. In particular, there are no observable reference points in the cheek areas, and none in the forehead area except possibly skin creases. When the talking head is that of a dark skinned person, the reconstructed image may show further degradation of subtle facial features.

Use of an IR camera in conjunction with a video camera, or use of a dualband camera at the transmission end offers the potential for marked improvements. Infrared minutiae are more numerous than visible markers and are present throughout the face, including areas of the cheeks and forehead and chin where no visible minutiae may be present. Therefore, modeling of the movements of infrared minutiae can provide finer detailed replication of expressions and speech than modeling based upon visual references.

At the transmitting end, a visual baseline image of the subject face is sent, followed by transmission of only the movement vectors of those infrared minutiae which move from frame to frame. At the receiving end, the baseline face is animated based upon overlaying the IR minutiae movements on the visual image.

Early results indicate a minimum of 150:1 compression for highly energetic faces, to 400:1 for mildly mobile faces when 30 frames per second are processed. A primary application for this technique is videoconferencing, where the goal is to provide acceptable quality imagery over dial-up lines, at acceptable cost.

Video e-mail and videophone could also utilize the significant bandwidth reduction and automated re-synchronization of voice and image.

By processing sequences of images taken from known expressions and/or known speech elements, a sequence of movements of infrared minutiae can be extracted which corresponds to that expression or speech element for that person or for persons in general. Subsequently, when the same sequence of movements of infrared minutiae is seen, it can be inferred that the person is displaying the same expression or speech element as during the initial sequence. This enables the automated determination of expression or speech, allowing for compression of transmitted video in conjunction with audio. The combination may offer additional composite compression and improved synchronization.

The same basic technique can also be used to create a dictionary of facial expressions and speech elements for use in animation of a synthetic face.

The talking head video compression system will have both video and IR cameras, and can be used to recognize and/or generate facial expressions and/or speech-related facial movements from the IR image and superimpose them on a contemporaneous visual image. The use of correlated infrared and video facial images offers significantly better fidelity of expression and speech-related variations in compression and reconstruction of talking head video, while also ensuring the authenticity of the related transmissions.

DETAILED DESCRIPTION

The preferred method for aligning and comparing images of the face and body from different images according to the invention will now be described.

The vascular system supplying the human face typically exhibits thermal variations on the order of 7° C. across the facial surface. Certain general features, such as hot patches in the sinus areas, relatively cool cheeks, and cold hair pertain to all facial thermograms. Other features such as specific thermal shapes in certain areas of the face are characteristic of a particular person.

Variations in temperature across the facial surface can be imaged by thermal cameras sensitive to wavelengths in the 3–5, 8–12, or 2–15 micron ranges. Current commercially available cameras provide thermal resolution of 0.025° C. and spatial resolution of better than 0.02", resulting in 65,000 to 265,000 discrete thermal measurements across the surface of the face. For most cameras, the thermal map is regenerated 30 times per second to produce either a standard video output which can then be recorded and processed on standard videotape equipment, or a direct digital signal which can be input to a computer.

Figure 1A:
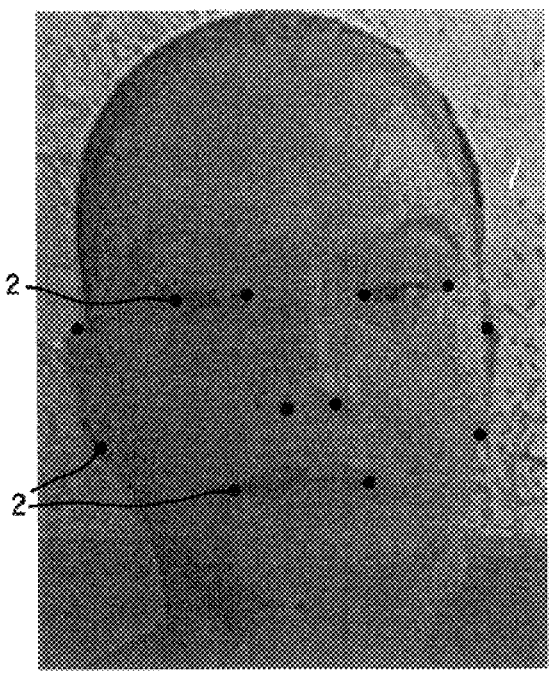
FIGS. 1a and 1b are a visual image and facial thermogram, respectively, taken of the same face from a distance of 15 feet showing coincident minutiae for each modality
Figure 1B:
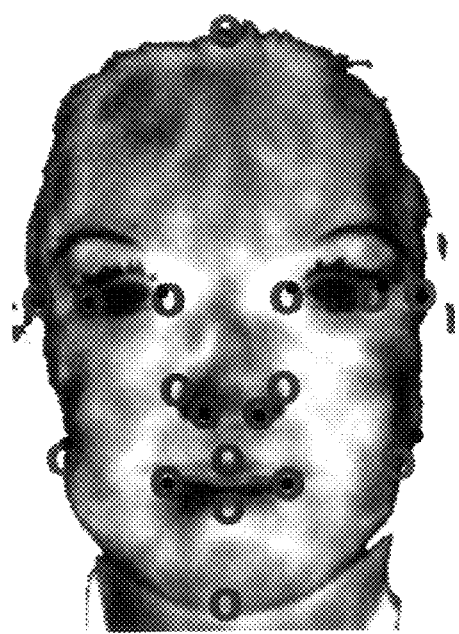
Figure 2A:
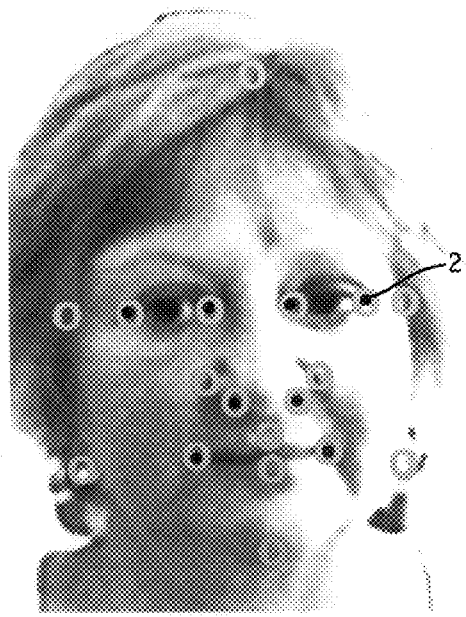
FIGS. 2a–2d are visual images of four different faces, respectively, showing coincident minutiae.
Figure 2B:
Figure 2C:
Figure 2D:
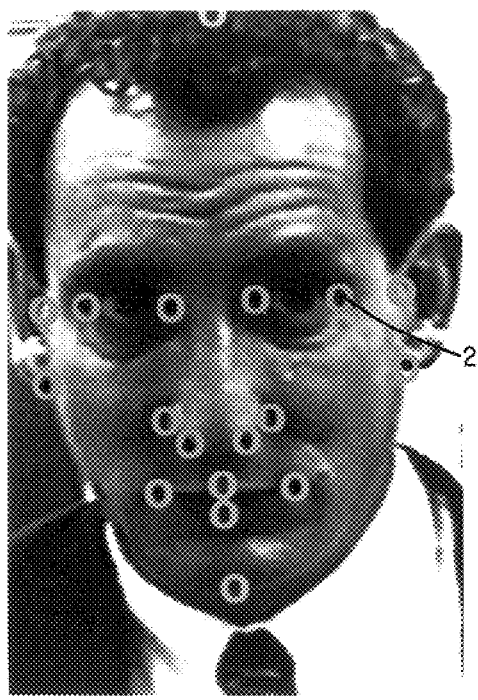
Figure 3A:
FIGS. 3a–3c are images of the vascular structure and feature images from infrared minutiae of the visual images of FIGS. 1a, 2a, and 2b, respectively, generated by thresholding the IR image and using all pixels hotter than threshold.
Figure 3B:
Figure 3C:

In FIGS. 1a and 1b, there are shown the visible and infrared images of the same individual taken via a conventional camera and an infrared camera, respectively. These images contain minutiae 2. Similarly, FIGS. 2a–2d are visual images of different people, each image having identifiable minutiae points 2. FIGS. 3a–3c are thermal or infrared images of the individuals shown in FIGS. 1a, 2a, and 2b.

In addition to branch points of superficial blood vessels, various other types of minutiae may be automatically extracted, including:

(1) the centroid of each constant thermal area;

(2) points of maximum curvature on constant thermal contours;

(3) anastomoses;

(4) lymph nodes, glands, other anatomical areas of distinguishable thermal capacitance;

(5) head outline and hairlines;

(6) scars, tattoos, and other marks which may or may not be visible in normal photographs;

(7) undefined locations generated by wavelet or fractal-based compression and expansion of the thermal image; and (8) apparent end points where the blood vessel goes too deep to be seen.

Use of various combinations of minutiae types can provide additional resolution and accuracy, and can also increase the security of identification systems by using a particular and undisclosed set of minutiae and characteristics.

Since every pixel in an IR image represents a thermal measurement of the skin at that corresponding location on the body, every pixel in an IR image can be considered a minutia. In particular, thresholding an IR image and considering all hotter points to be minutiae leads to a simple realization of the preferred embodiment of the invention. There is a tradeoff to be made in constructing operational systems based on this invention: whether to utilize fewer minutiae which are selected with more computational complexity, or to use more minutiae from less selective processing. The methods according to the invention are the same whether the analysis is done more at the minutiae-extraction stage or at the minutiae comparison stage.

Simply taking obvious facial feature landmarks such as head outline, hairlines, the center of each nostril, pupil spacing, and the corners of each eye, provides a rudimentary set of metrics for classification or verification of a face. The Tal U.S. Pat. No. 4,975,969 discloses such a method for identifying faces based upon a limited number of measurements between visible features such as the ends of the mouth and ratios between those measurements. According to Tal, no two persons have the same set of such measurements. However, variations in such measurements for a given individual at different times appear to often be larger than the variations between persons. Positive identification of individuals, especially when one individual is attempting to appear to be another, requires the matching of a greater number of minutiae points than are available in the video image. For high security applications, it is desirable that the number of minutiae points extracted be such that it is virtually impossible to locate two individuals who would have identical minutiae sets.

Figure 4:
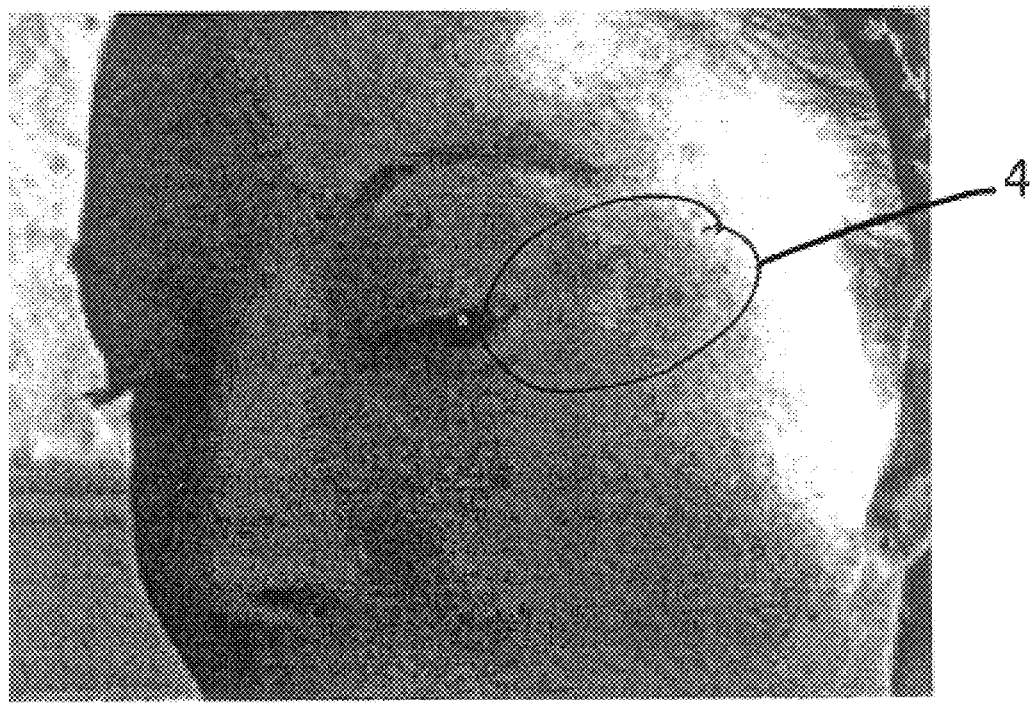
FIG. 4 is an infrared image of an individual with a scar which is not detectable in a visible image owing to make-up on the individual.

Scars 4, tattoos, and other marks which are visible in photographs should be selected as shown in FIG. 4. All related pixels can be used as visible minutiae, or a procedure can be established wherein certain features, such as the centroid, or outline, are selected as representative minutiae. The infrared image will in general contain more details than will the visible image. Particularly when the visible image is not high resolution, the IR image can be used to distinguish between brands and tattoos and temporary marks better than can a photograph. When makeup is worn, there may be no apparent visible mark.

Also, since it is of interest to identify faces seen in crowds, or faces turned at any angle, a significant number of minutiae points must be extractable for those applications so that even a partial face can be used for identification.

Comparison or alignment of sets of minutiae in two images requires a number of steps. First, the face axes are located. Overlaying the two sets of axes provides the initial approximate correspondence between two different images. In the full-frontal face, the thermal image is grossly symmetrical bilaterally. The canthi or sinus areas in normal individuals are the hottest extended areas of the face. When glasses are not worn, it is normally a simple process to locate the canthi in the thermal image and use them to establish axes for the face. Other features which may be used are the nostrils, which may present alternately hot and cold bilaterally symmetric areas as the individual breathes in and out. The horizontal axis is drawn through the pupils or canthi, which are readily distinguishable in the infrared images. The vertical axis is then drawn through the bow of the upper lip, or through the center point of the two nostrils, to the midpoint between the eyes. The intersection of the two axes occurs at the center of the two eyes which is defined as the center of the face. Axes for the visible face images are similarly drawn. Axes can be forced to be perpendicular. However, many people have an eyeline which is not perpendicular to the vertical axis of their head. Allowing the axes to vary in relative orientation preserves a useful identifying characteristic.

Next, all images are scaled to a standard size prior to comparison. If there is sufficient ground truth for all images in the database, the scaling is done in terms of actual size. In general, however, actual size cannot be precisely determined after the fact for all images in a database. Therefore the scaling is done by enforcing a standard distance between specific minutiae. For visible images, one good metric for scaling is the distance between pupils of the eyes. This distance is approximately the same for all adults at about 7 cm For infrared images, in which eye pupils cannot be distinguished, a good metric is the shortest line between canthi which is parallel to the horizontal axis of the face. This is approximately the same for all adults at about 3 cm.

Infrared minutiae are categorized as absolute if they are directly extractable from the thermal image, and derived if they result from some level of image transformation. Visible minutiae are all assumed to be absolute. Methods for their extraction are set forth below. Other methods may be used within the scope of this invention.

Infrared Minutiae

Infrared minutiae are selected. The number of minutiae obtained is a function of the sensitivity and resolution of the infrared camera. Candidate minutiae include:

1. Absolute minutiae directly extractable from the thermal image, such as: head outline, hairlines, branch points, and apparent end points of the superficial blood vessels.
2. Derived minutiae requiring processing of the image, including the following:

A. the centroid of each constant thermal area:

1. Where the digitized thermal image has N bits of grey scale, begin by dividing the image into two slices (thresholding) about the average grey value. The resulting image will have some number of areas of constant value. Locate the centroid of each, which is labeled as a minutiae point.
2. Increase the number of slices to 4, and repeat the above step, labeling the resulting centroids as minutiae.
3. Continue increasing the number of slices by a factor of 2, and labeling the resulting minutiae, until $2^{**}N$ slices are obtained.
4. If additional minutiae are desired, continue the process using odd numbers of slices.
5. The minutiae set consists of the centroids labeled as (x, y, z) where (x,y) is the location on the face relative to the face axes with (0,0) at the designated face center, and z is the corresponding thermal value.

B. the points of maximum curvature on constant thermal contours, either concave or convex cusps having less than a given radius of curvature.

1. Consider all thermal contours in the digitized image. If the data is considered noisy, reduce the number of grey levels to represent true differences in the thermal data.
2. Establish a radius of curvature such that any portion of any contour line which has a tighter curvature will generate a minutiae point.
3. The added minutiae set will consist of the maximum inflection points labeled as (x, y, z, a, D), where (x, y) is the location of the minutia point relative to the facial axes, z is the thermal value at that point, a is the angle subtended by a tangent to the thermal contour at the minutia point, and D is the range of thermal values (equal to the number of constant thermal contours crossed) between the minutia point and the centroid of its thermal contour.

C. run length encoding start and stop locations.

1. Perform run length encoding of the thermal image.
2. Each stop/start location generates a minutia point.
3. The added minutiae set will consist of the (x, y, z) value associated with those points.

D. undefined locations generated by compression and subsequent expansion.

1. Perform wavelet or fractal-based compression on the thermal image.
2. Expand the compressed image and compare it with the original.
3. The added minutiae set will consist of the undefined locations and will be labeled as (x, y, z,w) where (x,y) is the location of the point relative to the facial axes, z is the thermal value at that location in the original thermal image, and w is a set of wavelet coefficients.

E. All pixels above a selected threshold, of all pixels within a selected thermal range and distance from other defined pixels.

Visible Minutiae

Visible minutiae are selected depending on the resolution, contrast, and clarity of the visible images. Candidate minutiae include: head outline, hairlines, pupils, eye inner and outer corners, nostrils, mouth corners, lip bow, and tip of nose.

Tables are then created of the infrared minutiae and the visible minutiae. Table entries include the locations of each minutiae relative to the face axes. Coincident minutiae are linked either manually or automatically. Coincident minutiae include: pupils, inner and outer eye corners, nostrils, head outline, hairlines, and ear—head connection points.

After selection of coincident minutiae, they are matched. Various perturbations, such as facial expression changes, can distort the relative locations of minutiae points to an extent. This is analogous to the deformations which occur in fingerprints due to movement between the fingers and the print surface. The minutiae matching algorithms allow for variations in the position and characteristics of the minutiae, as well as in the subset of minutiae which are seen due to the field of view of the camera and to possible obstruction of certain areas of the face in the image. The difference between locations of available coincident minutiae is calculated relative to the face axes. Different methods can be used to evaluate the difference between the two sets of minutiae.

One such method is standard graph matching, with tolerances established for errors due to imperfect knowledge of head position and distance, and errors associated with treating the head/face as a two-dimensional surface or as a sphere, and errors associated with residual errors even if a true three-dimensional model of the head is made, using laser interferometry or other techniques.

Another method is Flash Correlation® as described in the Prokoski U.S. Pat. No. 5,583,950. Large circular areas at each minutiae location are used, where the size of the area or dot represents the uncertainty associated with the exact minutiae location, due to facial expression changes, camera resolution, and other factors.

A further method for evaluating the difference between two sets of minutiae is analogous to fingerprint minutiae, using any of the many minutiae comparison techniques developed to compare location and characteristics of sets of minutiae.

Figure 5A:
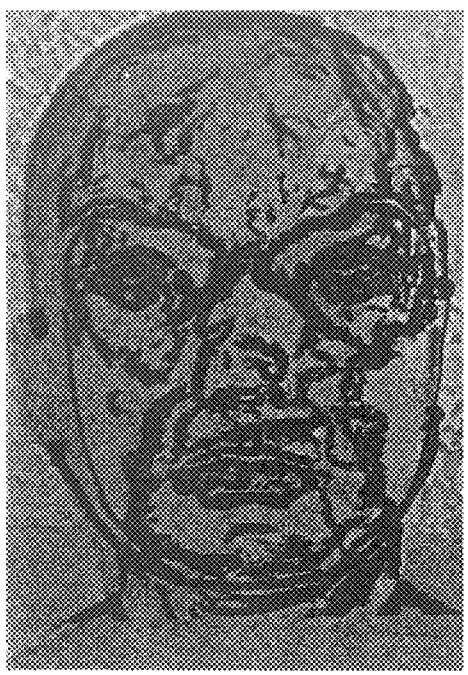
FIG. 5a illustrates an overlay of the IR image of FIG. 3a onto the corresponding visual image of FIG. 1a to illustrate the alignment of coincident minutiae.
Figure 5B:
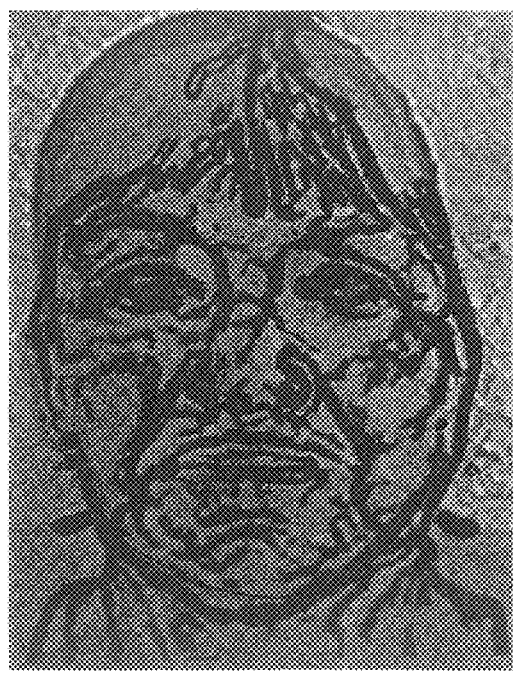
FIG. 5b illustrates an overlay of the IR image of FIG. 3b onto the visual image of FIG. 1a to illustrate the misalignment of coincident minutiae.

In FIGS. 5a and 5b, matching of coincident minutiae is illustrated. More particularly, in FIG. 5a, the infrared image of FIG. 3a is overlaid onto the corresponding visual image of FIG. 1a to illustrate the alignment of coincident minutiae and thus a match of individuals. In FIG. 5b, the infrared image of FIG. 3b is overlaid onto the visual image of FIG. 1a to illustrate the misalignment of coincident minutiae, thus indicating no match of the individuals.

For high security applications or where the database subjects may have been disguised, may have aged or changed their weight or appearance, the matching algorithm considers such possible variations in deciding possible matches.

Whichever minutiae extraction and comparison techniques are used, they produce a metric which can be compared to a threshold which is set or determined adaptively by considering databases where the images are of known persons. The threshold (CM) is set for the desired trade off of the rates of false positive and false negative results.

If consideration of coincident minutiae leads to the conclusion that a match is possible, that decision can be refined by consideration of the spectrum-dependent minutiae. The two images are optimally aligned according to the face axes, and warped so that the coincident minutiae are overlaid. Then each spectrum-dependent minutiae is considered relative to a rule which relates it to the other image. The rule also assigns a point value to the degree of compliance with the rule. Next the system confirms adherence or violation of the rules and computes the cumulative score associated with all of the rules.

An Exclusion Test is the simplest rule. It states that no vascular structure or minutiae seen in the IR image can be overlaid outside the head outline of the visual image, or inside of the eye, mouth or nostril areas.

Anatomical rules including the following:
1. the facial vein and the facial artery must lie outside nose boundaries, must not go through mouth or eyes or nostrils, and must be inside the face from the ears;
2. the supraorbital and opthalmic arteries must lie above the eyes;
3. the transverse facial vein and artery must lie below the eyes;
4. the transverse vein must lie inside face area between the eyes, and outside the area of the nose; and
5. the labial vein and artery must surround the mouth.

A particular class of problems which is of interest includes images taken over long periods of time, whether of children or adults. In these cases, the set of coincident minutiae and the rules governing spectrum-dependent minutiae will vary to accommodate anatomical changes associated with growth and aging. Either of the images being compared may be artificially aged to the other, prior to minutiae being extracted for comparison.

From the standpoint of evidentiary use, it might be argued that the application of eigenanalysis to a very large database of faces, such as all mug shots in the FBI files, would be considered so esoteric by the public at large that automated matches based upon its use will not readily be acceptable to a jury as convincing evidence of identity. By comparison, the proposed facial minutiae matching technique, being analogous to fingerprint identification, is expected to find a more understanding reception by the law enforcement community, and to be more acceptable for evidentiary purposes within a reasonable number of years after its introduction.

Figure 6A:
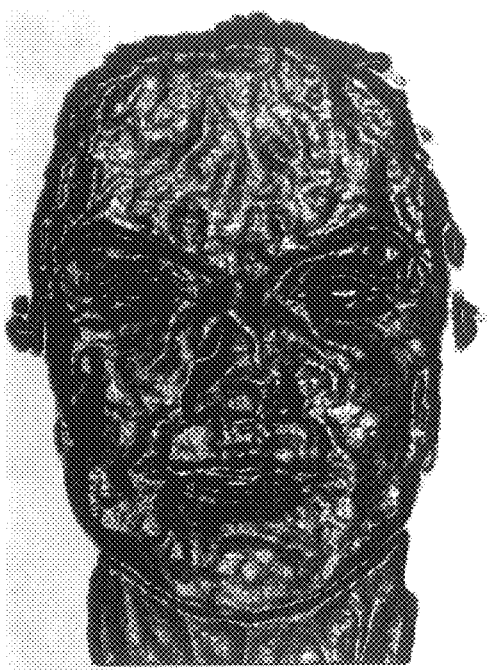
FIGS. 6a–6c are thresholded infrared images of the frontal face, side face, and neck, respectively, of an individual taken with an indium antimonide focal plane array camera.
Figure 6B:
Figure 6C:
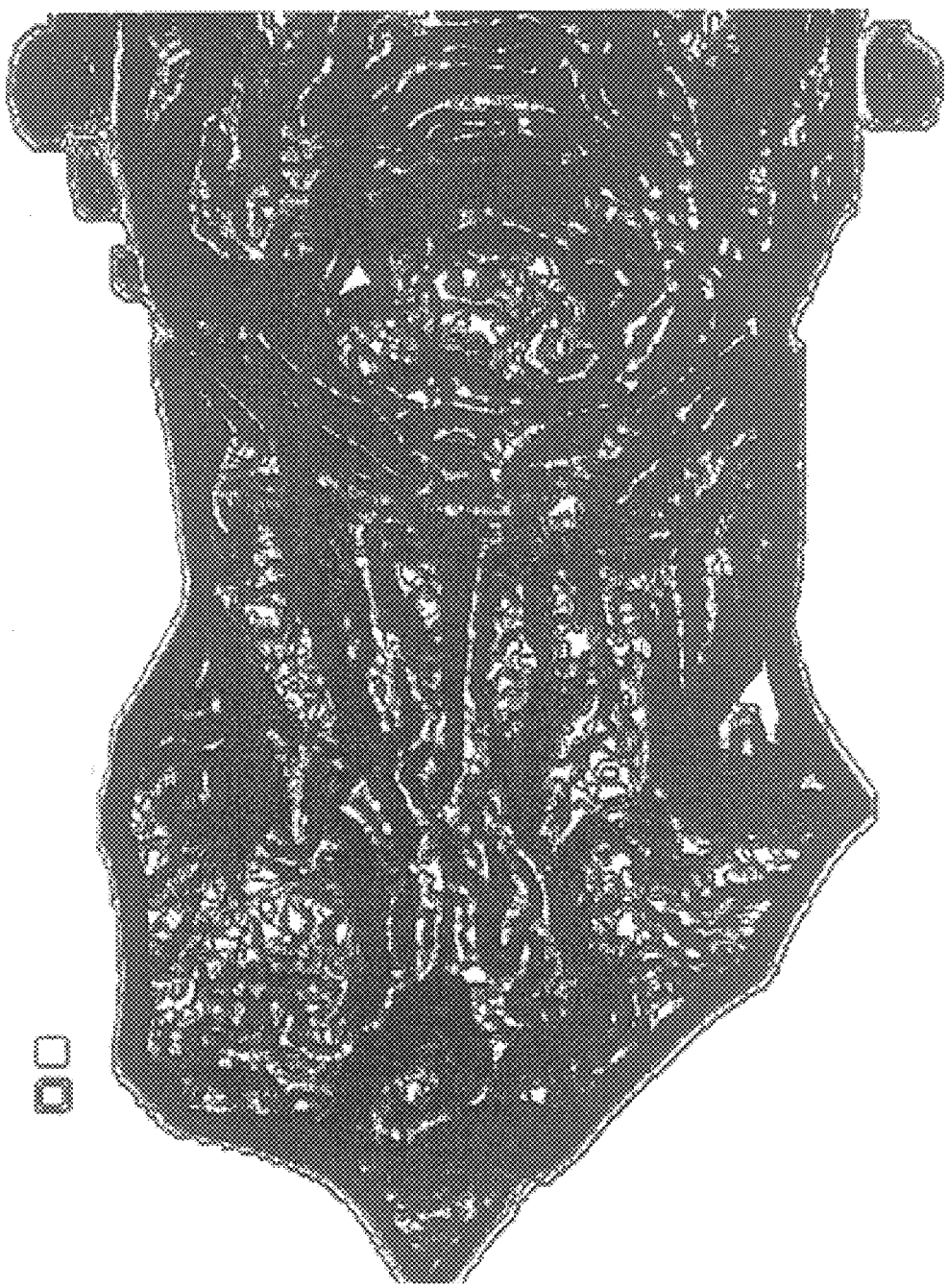

A threshold is set or determined adaptively, such that pairs of images having a calculated value within the threshold are considered to be possible matches. The decision algorithm utilizes a cumulative rule score or simply exclude any image which breaks any rule. The quality of the imagery used, and the possibility of disguise will be considered in establishing the decision algorithm to determine possible or impossible matches. FIGS. 6a–6c show the threshold infrared image of the front face, side face, and neck of an individual.

Two alternative embodiments of the method for aligning and comparing images of the face and body from different images according to the invention will now be described.

For compression of talking head video, a dualband IR/visual camera is used. The processor at the transmitting end continuously extracts IR minutiae from each frame of the IR video. It locates and tracks the face axes, detecting when there is significant head movement. A visual baseline image of the subject is sent, followed by transmission of only the movement vectors of those infrared minutiae which move from frame to frame. If significant head movement occurs, then a new baseline video image is transmitted, followed again by transmission sequences of only the movement vectors.

At the receiving end, the baseline face is animated based upon overlaying the IR minutiae movements on the visual image. Morphing techniques are used to smooth the transition to a new baseline image. If the morphing indicates too much change in the new baseline, then a signal is sent back to the transmission end to reduce the allowed head movement before a new baseline is transmitted. The technique allows for greater bandwidth compression for talking heads with little movement, while allowing automated accommodation of very mobile faces. Separate IR and visual cameras can be used, but the processing time required is greater.

Figure 7B:
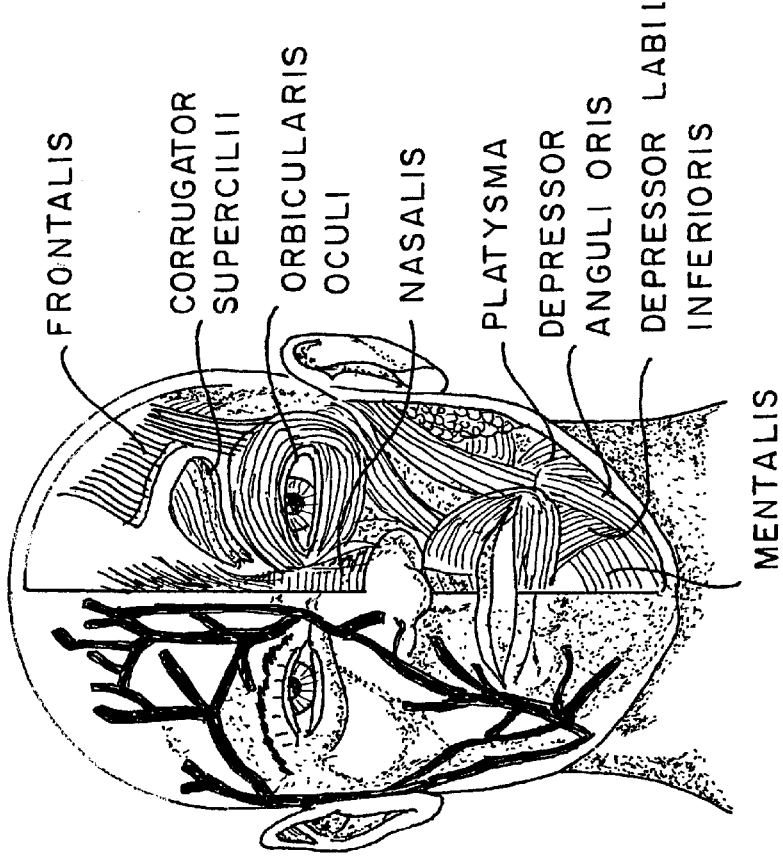
FIGS. 7a and 7b are images of vascular structure minutiae for an individual smiling and frowning, respectively.
Figure 7A:
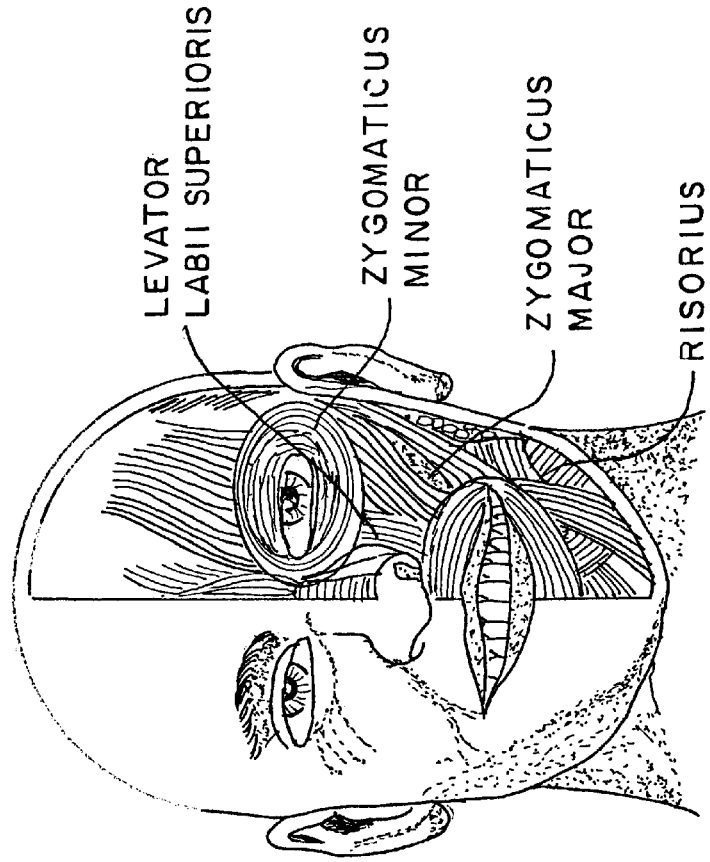

Muscles of the face involved in facial expression and speech are shown in FIGS. 7a and 7b. Change in expression or action of speech causes movements in affected areas of the face, distorting the locations of the infrared spectral-dependent minutiae, and also distorting visible minutiae. However, the infrared minutiae are more numerous and are present in areas where no visible minutiae are present. Therefore, modeling of the infrared minutiae provides finer detailed modeling of expressions and speech than does modeling based upon visual minutiae.

Based upon processing sequences of images taken during known expressions and/or known speech elements, a sequence of movements of infrared minutiae can be extracted which corresponds to that expression or speech element for that person.

Subsequently, when the same sequence of movements of infrared minutiae is seen, it can be inferred that the person is displaying the same expression or speech element as during the initial sequence. This enables the automated determination of expression or speech, allowing for compression of transmitted video. A baseline image of the person can be transmitted, and then a code for the expression or speech element is transmitted. At the receive end, the expression or speech element is reconstructed and a simulated animation of the face presented.

This technique can also be used to create a dictionary of facial expressions and speech elements for use in animation of a synthetic face.

Figure 8:
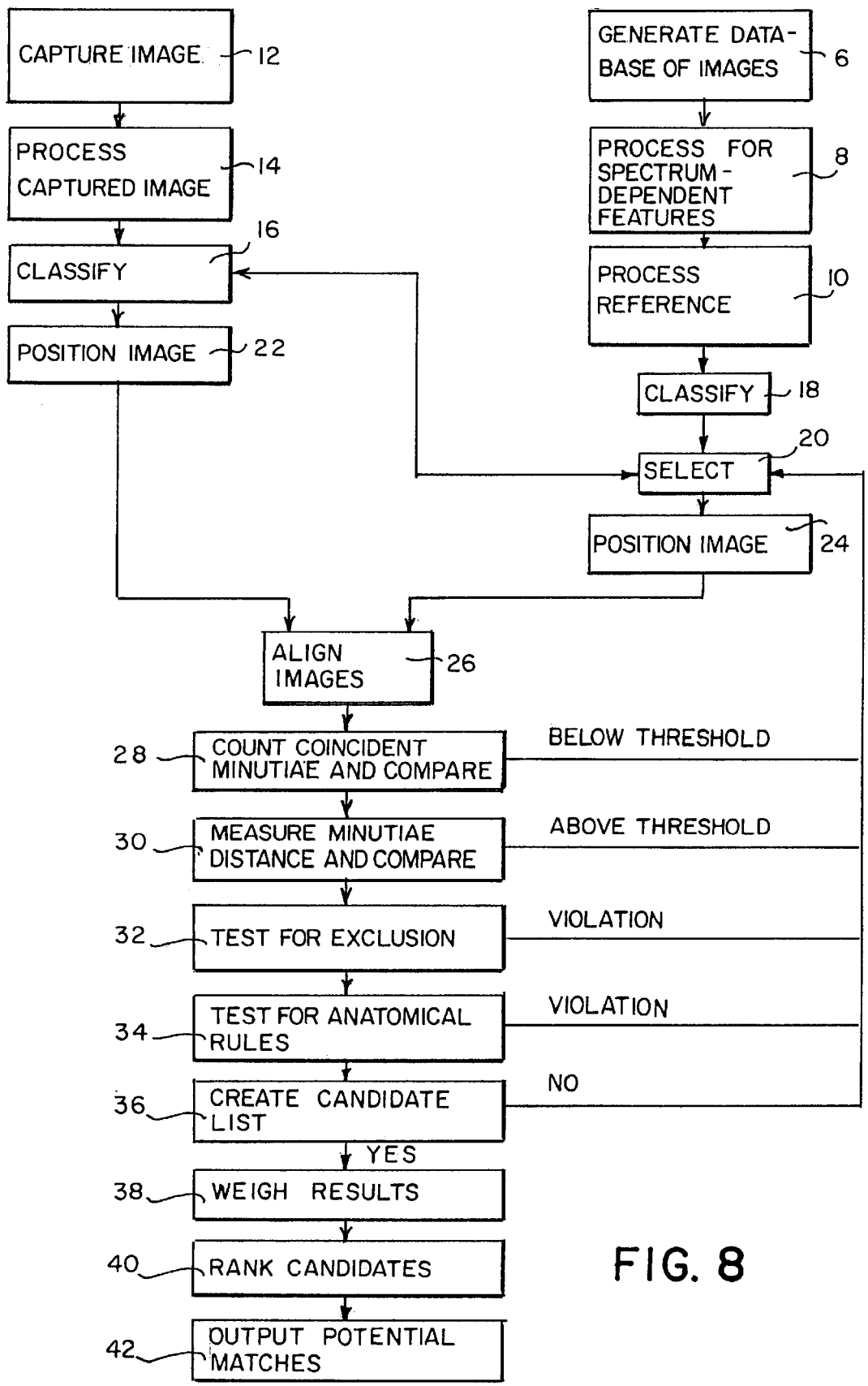
FIG. 8 is a flow diagram showing the method according to the invention.

An overview of the method of the invention will be described with reference to FIG. 8.

First, a database of images of known individuals is generated 6. The images can include infrared, visual, hyperspectral images, or medical images which have been annotated with infrared minutiae. Each image is scaled to a common reference. Next, the images in the database are processed for spectrum-dependent features and minutiae 8. The processing locates IR minutiae annotated onto other sensor images, assigns face axes, counts the number of minutiae, tags the image with the resulting data, and assigns a quality measure to the image based on the number of minutiae identified and the quality thereof based on the minutiae extraction process. In the process reference step 10, selected images of a threshold quality are stored.

The image of an unknown individual is captured 12 using an infrared camera or other sensor. This image is processed 14 to locate the face axes, scale the image, locate IR minutiae, and assign a quality measure similar to the process step 8.

The captured image is classified 16 as is the database image 18 to reduce search time. Appropriate classification techniques include the use of principal component parameters or symmetry waveforms when both captured and reference databases include only IR images; coincident minutiae metrics when both databases include only IR and visual images; or IR minutiae metrics when both databases include images annotated with IR minutiae. Specific application of a classification technique will depend on the size of the database. Using distance metrics computed from coincident IR and visual minutiae, for example, twelve measurements may be taken which are the same in both IR and visual images. Very large databases can be partitioned effectively using such metrics.

Figure 9A:
FIGS. 9a and 9b are illustrations of two different visual images overlaid with a thermal image of vascular minutiae showing a match and mismatch, respectively.
Figure 9B:

Next, the classified captured image and the database images are compared to select a potential match 20 from the database. If no potential matches are found, this is the end result. However, if a potential match is found, further processing occurs to verify a match. The captured image is positioned 22 to determine the rotation, tip and tilt thereof. The database image is similarly positioned 24. If necessary, corrections in position are made so that the images to be compared are similarly oriented. Next, the captured and database images are overlaid in alignment 26. This is shown in FIGS. 9a and 9b. The distances between coincident minutiae (those which occur in both image modes) are calculated. For each minutiae area of the face, an error band is established which represents the possible variation in position of that minutiae due to facial expression change or speech-related movement.

Those pairs of coincident minutiae where the captured and database images minutiae are both within the error band of the other are counted 28. The count is compared to a pre-established threshold. If the count is below the threshold, that database image is not considered a possible match and the next sequential image from the database is selected 20 for comparison. If the count is equal to or greater than the threshold, the process continues.

Next, the composite distance between pairs of coincident minutiae are measured and compared to a pre-determined threshold 30. If the measure is greater than the threshold, that database image is not considered a possible match and the next sequential image from the database is selected 20 for comparison. If the measure is equal to or less than the threshold, the process continues.

Next, an exclusion zone for the database image is established 32 in which the eyes, nostrils, mouth, and outside boundaries of the face are set as exclusion zones to form a mask of the database image. The mask is aligned with and superimposed on the captured image. If any IR minutiae in the captured image fall within the exclusion zones, it is considered a violation, and that database image is no longer considered a possible match and the next image is selected. If no violations occur, the process continues with testing for anatomical rules 34 governing where specific IR minutiae may be located. Those rules are tested against the database images using the captured image. For example, the facial artery must lie between the nose and the ear. When the captured and database images are aligned and overlaid, each anatomical rule is tested. Any violation results in that database image no longer being considered and the next image is selected. If no violations occur, the process continues.

From the database images which progress through the processing steps, a candidate list is created 36. The results are weighed 38 in accordance with certain factors such as the database size and completeness. For example, if the database in known to include several images of all employees of a company, that fact will influence the reliability of a match when multiple database images of the same person are found as possible matches to the captured image.

Based on the weighed results, the candidate matching images from the database are ranked 40 and output 42.

Figure 10:
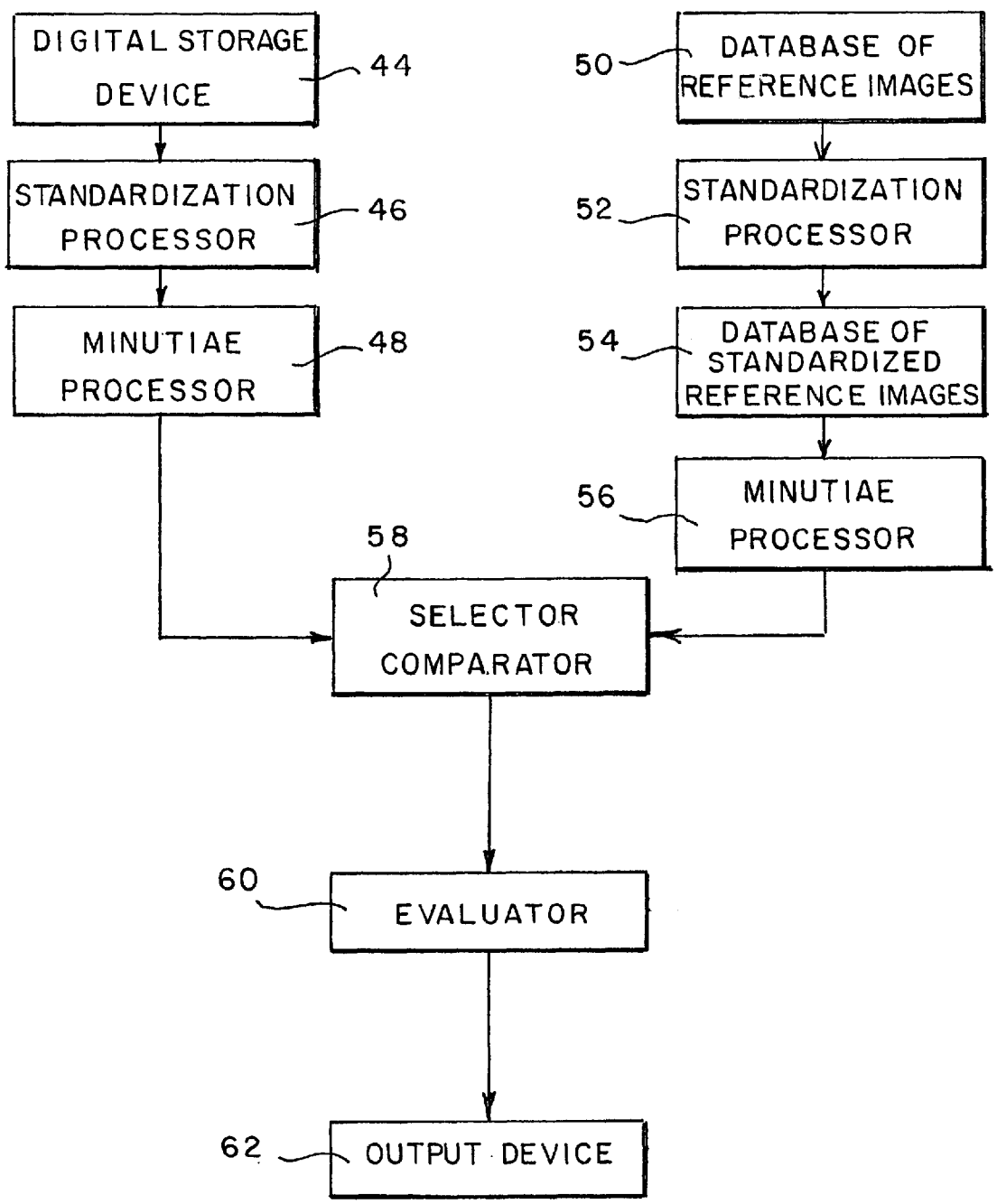
FIG. 10 is a block diagram showing the apparatus according to the invention.

The apparatus according to the invention will be described with reference with FIG. 10. The apparatus includes a digital storage device 44 for the capture of infrared images. Connected therewith is a standardization processor 46 which standardizes the image and a minutiae processor 48 which extracts and analyzes minutiae for each IR image.

The apparatus also includes a digital database 50 which stores a plurality of reference images. A standardization processor 52 standardizes the images which are delivered to a database 54 containing standardized reference images. A minutiae processor 56 extracts and analyzes spectrum independent minutiae and IR minutiae superimposed on medical images.

The minutiae processor 48 for the captured image and the minutiae processor for the database image are connected with a selector comparator device 58 which determines whether a match exists between the images to identify the individual from which the captured image was taken. More particularly, the selector aligns the images to determine if there is an initial match. If not, the comparator compares the coincident minutiae within the images. A first comparison is made by counting the number of coincident minutiae. If the number exceeds a predetermined threshold, the processing continues. If the threshold count is not reached, then the database image is rejected and the next image in the database is selected for comparison. A second comparison is made of the measured distance between coincident minutiae. If the distance exceeds a threshold, the database image is rejected and the next database image is selected for comparison. If the measured distance is below the threshold, processing continues.

An evaluator 60 tests the database image for exclusion zones and anatomical rules. If any minutiae of the captured image fall within the exclusion zone, a violation occurs and the database image is rejected. The anatomical rules specify where specific infrared minutiae may be located. When the captured and database images are overlaid and aligned, each anatomical rule is tested. If a violation occurs, the database image is rejected.

The database images which pass through the comparison and evaluation stages are weighed according to the strength of match. The ranked potential matches are then output through the output device 62.

The method and apparatus of the invention can be extended to the comparison of images other than visual images such as, for example x-rays or sonograms. The x-ray and sonogram images can be aligned by first annotating each with coincident IR minutiae, then morphing the two sets of IR minutiae as overlays onto the medical images, or morphing each medical image to a standard IR image. The morphing can be in three dimensions when depth information is provided for the IR minutiae.

What is claimed is:

1. A method for aligning anatomical images taken from first and second different spectral bands, comprising the steps of
   (a) identifying minutiae in a first anatomical image which are dependent upon the first spectral band thereof, said first spectral band comprising a visual band;
   (b) identifying minutiae in a second anatomical image which are dependent upon the second spectral band thereof, said second spectral band comprising an infrared band;
   (c) identifying coincident minutiae which occur in said first and second anatomical images and which correspond to characteristic features of the anatomical images; and (d) morphing one anatomical image to the other anatomical image to overlay the coincident minutiae, whereby the anatomical images are in alignment.

2. A method as defined in claim 1, and further comprising the step of calculating the degree of morphing required to achieve optimal alignment, said morphing step including the steps of stretching, warping, and shrinking said one image with respect to said other image.

3. A method for identifying an unknown person from a first anatomical image taken in a first spectral band by comparing it with a plurality of second anatomical images of known persons taken in a second different spectral band and stored in a database, said first and second spectral bands comprising visual and infrared bands, comprising the steps of (a) identifying minutiae in each anatomical image which are dependent upon the spectral band thereof;

(b) identifying coincident minutiae which occur in the anatomical images and which correspond to a characteristic feature of the images;

(c) overlaying the coincident minutiae by morphing said first anatomical image onto each of said second anatomical images, (d) selecting one of said second anatomical images requiring the least morphing as the most likely matching anatomical image from said database and eliminating the remaining second anatomical images; and (e) comparing the degree of morphing with a threshold to determine whether the match is sufficient to identify the unknown person as one from the database.

4. A method as defined in claim 3, and further comprising the stop of assigning a level of confidence to the match based on the difference between the threshold and the degree of morphing.

5. A method as defined in claim 3 and further comprising the steps of (f) selecting those second images which have a degree of morphing within the threshold as possible matches to the first image;

(g) establishing exclusion zones for the second images;

(h) determining whether any features of the first image extend into the exclusion zones of the second images when they are aligned and overlaid;

(i) discarding from further consideration any second images whose exclusion zones are violated by the first image;

(j) considering any remaining second images as possible candidates for matching the first image;

(k) rank ordering the possible candidates by the degree of morphing required; and (l) adjusting the rank to accommodate multiple second images of the same person.

6. Apparatus for aligning anatomical images taken from first and second different spectral bands, comprising (a) means for generating a first anatomical image from a visual spectral band;

(b) means for generating a second anatomical image from an infrared spectral band;

(c) means for identifying coincident minutiae which occur in both anatomical images and which correspond to a characteristic feature of the anatomical images; and (d) means for overlaying the coincident minutiae by morphing one anatomical image to the other anatomical image to compare the coincident minutiae and determine whether there is a match of the two anatomical images.

7. Apparatus as defined in claim 6, and further comprising means for calculating the degree of morphing required to achieve optimal alignment, said overlaying means stretching, warping, and shrinking said one image with respect to said other image.

8. Apparatus as defined in claim 7, wherein said image generating means comprise a camera for generating a visual image and an infrared camera for generating an infrared image.

9. Apparatus as defined in claim 8, and further comprising a database for storing a plurality of visual images of known individuals whereby an image from an unknown individual can be compared with said stored images to identify the unknown individual.

10. A method for identifying an unknown person from a first image taken in one spectral band by comparing it with a plurality of second images of known persons taken in a different spectral band and stored in a database, comprising the steps of (a) identifying minutiae in each image which are dependent upon the spectral band thereof;

(b) identifying coincident minutiae which occur in the images and which correspond to a characteristic feature of the images;

(c) overlaying the coincident minutiae by morphing said first image onto each of said second images;

(d) selecting one of said second images requiring the least morphing as the most likely matching image from said database;

(e) comparing the degree of morphing with a threshold to determine whether the match is sufficient to identify the unknown person as one from the database;

(f) selecting those second images which have a degree of morphing within the threshold as possible matches to the first image;

(g) establishing exclusion zones for the second images;

(h) determining whether any features of the first image extend into the exclusion zones of the second images when they are aligned and overlaid;

(i) discarding from further consideration any second images whose exclusion zones are violated by the first image;

(j) considering any remaining second images as possible candidates for matching the first image;

(k) rank ordering the possible candidates by the degree of morphing required;

(l) adjusting the rank to accommodate multiple second images of the same person;

(m) establishing a set of anatomical rules which govern the relative location of minutiae from the two spectral bands;

(n) testing each of the possible candidates against each of the rules applied to the first image;

(o) eliminating from further consideration any candidate which violates any rule;

(p) assessing the number of remaining candidates;

(q) adding additional anatomical rules if a further reduction is required;

(r) testing each remaining candidate against the added rules;

(s) rank ordering the possible candidates by the degree of morphing required; and (t) adjusting the rank to accommodate multiple second images of the same person.

11. Apparatus for identifying an unknown person from a first anatomical image taken in one of a visual and infrared spectral band by comparing it with a plurality of second anatomical images of known persons taken in the other of a visual and infrared spectral band and stored in a database, comprising:

(a) a digital storage device for the capture of first anatomical images;

(b) a first processor which standardizes the first anatomical images;

(c) a database of standardized second anatomical images considered as potential candidate matches to the first anatomical image;

(d) a second processor which extracts and analyzes spectrum-dependent minutiae of each anatomical image;

(e) a selector which aligns the first and second anatomical images;

(f) a comparator which matches coincident minutiae from the first and second anatomical images and excludes some second anatomical images as possible matches based upon the morphing required to overlay the coincident minutiae;

(g) anatomical rules encoded into image comparison steps;

(h) an evaluator which tests the first anatomical image for exclusion zones and anatomical rules relative to the second anatomical image and excludes as possible candidate matches those second anatomical images which fail the tests;

(i) a rank ordering processor which calculates the probability each candidate is a match, based upon the degree of processing and morphing required; and (j) output means for outputting said anatomical images, a rank ordering list, and confidence measures.

* * * * *